(12) United States Patent
Anzai et al.

(10) Patent No.: US 8,858,618 B2
(45) Date of Patent: Oct. 14, 2014

(54) STENT (75) Inventors: Takao Anzai, Fujinomiya (JP); Yosuke Kuruma, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 288 days.

(21) Appl. No.: 13/496,744

(22) PCT Filed: Sep. 6, 2010

(86) PCT No.: PCT/JP2010/065233
§ 371 (c)(1),
(2), (4) Date: Apr. 20, 2012

(87) PCT Pub. No.: WO2011/033957
PCT Pub. Date: Mar. 24, 2011

(65) Prior Publication Data
US 2012/0197385 A1  Aug. 2, 2012

(30) Foreign Application Priority Data
Sep. 18, 2009 (JP) ................. 2009-217285

(51) Int. Cl.
*A61F 2/82* (2013.01)
*A61F 2/91* (2013.01)
*A61L 31/10* (2006.01)
*A61L 31/16* (2006.01)

(52) U.S. Cl.
CPC .......... *A61L 31/10* (2013.01); *A61F 2250/0067* (2013.01); *A61F 2/91* (2013.01); *A61F 2/82* (2013.01); *A61F 2210/0061* (2013.01); *A61L 31/16* (2013.01)
USPC .......... 623/1.46; 623/1.42; 623/1.49

(58) Field of Classification Search
CPC ..... A61F 2/82; A61F 2210/0061; A61F 2/89; A61F 2/90; A61F 2/91; A61F 2/915; A61F 2/92
USPC ............. 623/1.42, 1.44, 1.45, 1.46, 1.49
See application file for complete search history.

(56) References Cited

U.S. PATENT DOCUMENTS

| | | | |
|---|---|---|---|
| 5,464,650 A | 11/1995 | Berg et al. | |
| 5,624,411 A | 4/1997 | Tuch | |
| 5,679,400 A | 10/1997 | Tuch | |
| 5,837,008 A | 11/1998 | Berg et al. | |
| 6,388,047 B1 | 5/2002 | Won et al. | |
| 6,583,219 B2 | 6/2003 | Won et al. | |
| 6,716,445 B2 | 4/2004 | Won et al. | |
| 6,833,004 B2 * | 12/2004 | Ishii et al. | 623/1.15 |
| 7,351,430 B2 * | 4/2008 | St. John et al. | 424/489 |
| 2002/0161169 A1 | 10/2002 | Won | |
| 2003/0008971 A1 | 1/2003 | Won | |
| 2003/0153887 A1 | 8/2003 | Nawata | |

(Continued)

FOREIGN PATENT DOCUMENTS

| | | |
|---|---|---|
| EP | 1019107 | 7/2006 |
| JP | 8033718 | 2/1996 |
| JP | H11500047 | 1/1999 |

(Continued)

*Primary Examiner* — David Isabella
*Assistant Examiner* — Suba Ganesan
(74) *Attorney, Agent, or Firm* — Day Pitney LLP

(57) ABSTRACT

Provided is a stent wherein the water-swellable polymer fine particles applied thereto rarely peel off even when the stent is deformed or when the water-swellable polymer fine particles are swollen. A stent wherein a plurality of water-swellable polymer fine particles are chemically fixed on the stent surface in a dispersed state is provided.

6 Claims, 4 Drawing Sheets

(A)

(B)

(56) References Cited

U.S. PATENT DOCUMENTS

2007/0178786 A1  8/2007  Nawata
2007/0299504 A1  12/2007  Gale
2009/0136736 A1  5/2009  Nawata
2010/0273647 A1  10/2010  Nawata

FOREIGN PATENT DOCUMENTS

| JP | 2002513627 | 5/2002 |
| JP | 2005-334654 | 12/2005 |
| WO | 92/11896 | 7/1992 |
| WO | 02085959 | 10/2002 |

* cited by examiner

STENT

The present application is based on PCT application No. PCT/JP2010/065233 filed on Sep. 6, 2010; and Japanese Patent Application No. 2009-217285 filed in the Japanese Patent Office on Sep. 18, 2009, the entire contents thereof being cited herein by reference.

TECHNICAL FIELD

The present invention relates to a stent, more particularly to a stent wherein water-swellable polymer fine particles disposed on the stent would not peel off even when the stent is deformed or when the polymer fine particles are swollen.

BACKGROUND

Putting a stent indwelling in a blood vessel has been practiced for treating a heart disease or the like. In general, the material constituting a stent is a metallic material such as stainless steel, a cobalt-chromium alloy and a nickel-titanium alloy. After the stent is put indwelling in a blood vessel, a series of healing process such as growth of smooth muscle cells and formation of an endoththeliocyte layer proceeds following to a thrombogenic reaction and an inflammation reaction. In recent years, drug-eluting stents for the purpose of preventing excessive growth of smooth muscle cells or intravascular restenosis arising from the stent placement have been developed and put to clinical use. Such a drug-eluting stent has a structure in which a surface thereof is coated with a hydrogel polymer such as polyacrylic acid (see, for example, WO-A1-92/11896).

The stent as described in the above Patent Document WO-A1-92/11896 has its surface entirely coated with the hydrogel polymer. When such a stent is put in a physiological environment (particularly, in a blood vessel), expansion of the stent and swelling of the hydrogel polymer occur simultaneously, and the hydrogel polymer particles come into contact with each other, resulting in an excessive increase in volume. Therefore, strains are generated between the stent and the hydrogel polymer, whereby the hydrogel polymer is caused to peel off the stent and flow out into the blood vessel.

SUMMARY

The present invention has been made in consideration of such a problem as described above in relation to the example given of WO-A1-92/11896.

Accordingly, it is an object of the present invention to provide a stent such that water-swellable polymer fine particles would rarely peel off even when the stent is deformed or the polymer fine particles are swollen.

In consideration of the above-mentioned problem, the present inventors made intensive and extensive investigations. As a result of their investigations, the present inventors found out that the above-mentioned problem can be solved by a method in which a plurality of water-swellable polymer fine particles are chemically fixed on a surface of a base material of a stent in a dispersed state.

Accordingly, the present invention provides a stent wherein a plurality of water-swellable polymer fine particles are chemically fixed on a stent surface in a dispersed state.

According to the stent according to the present invention, the plurality of water-swellable polymer particles are chemically fixed on the stent surface in a dispersed state. This ensures that even when the stent is expanded and is deformed, no strain is generated in the water-swollen polymer fine particles, so that breakage or peel-off of the polymer fine particles would rarely occur.

In addition, the stent according to the present invention shows little adhesion of platelets thereto and is, therefore, excellent in antithrombogenic properties.

DETAILED DESCRIPTION

The stent according to the present invention is characterized in that a plurality of water-swellable polymer fine particles are chemically fixed on a surface of the base material of the stent in a dispersed state.

Figure 1:
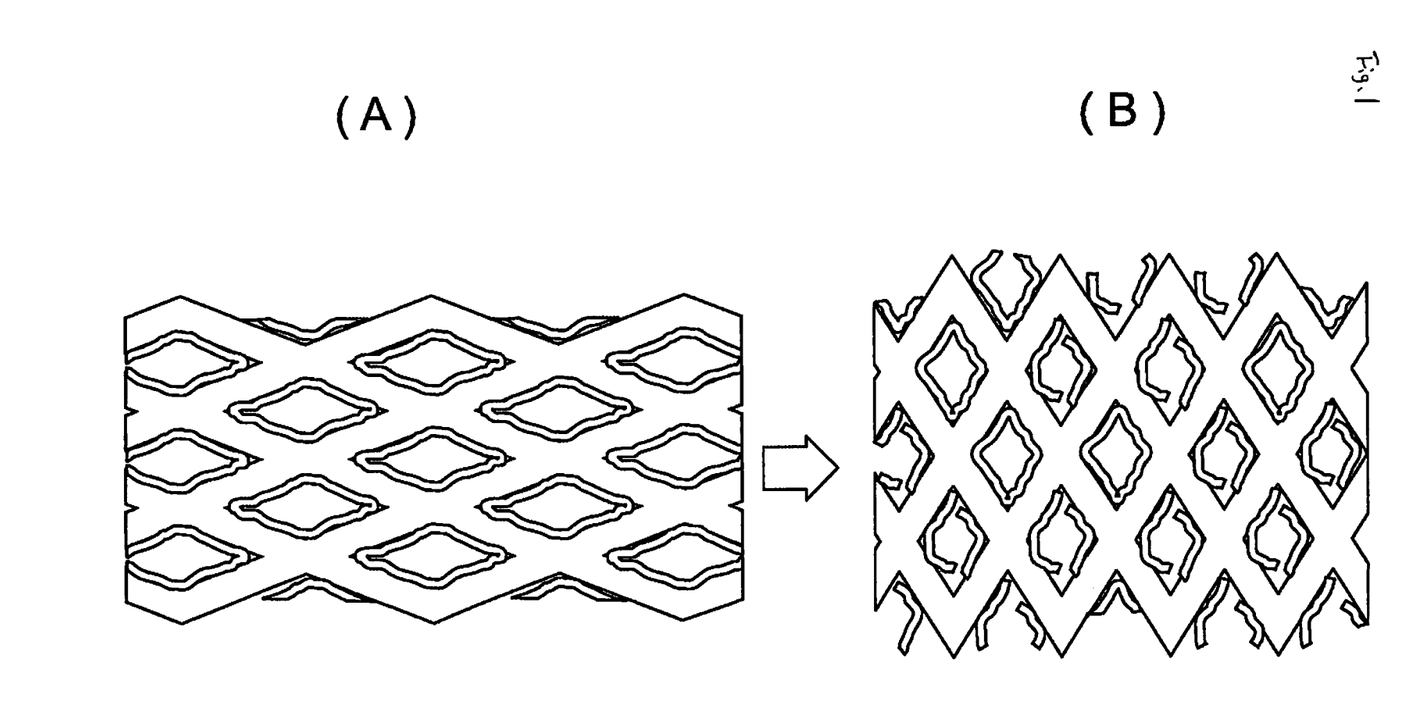
FIG. 1 shows schematic views illustrating a conventional stent, wherein (A) is a schematic view of the stent before expansion, and (B) is a schematic view of the stent after expansion.

FIG. 1 shows schematic views illustrating a conventional stent the surface of which is entirely coated with a hydrogel polymer, wherein (A) is a schematic view of the stent before expansion and (B) is a schematic view of the stent after expansion. As shown in (B) of FIG. 1, when the stent is expanded and deformed, strains are generated between the stent and the swelled hydrogel, whereby the hydrogel is broken and peels off the stent.

Figure 2:
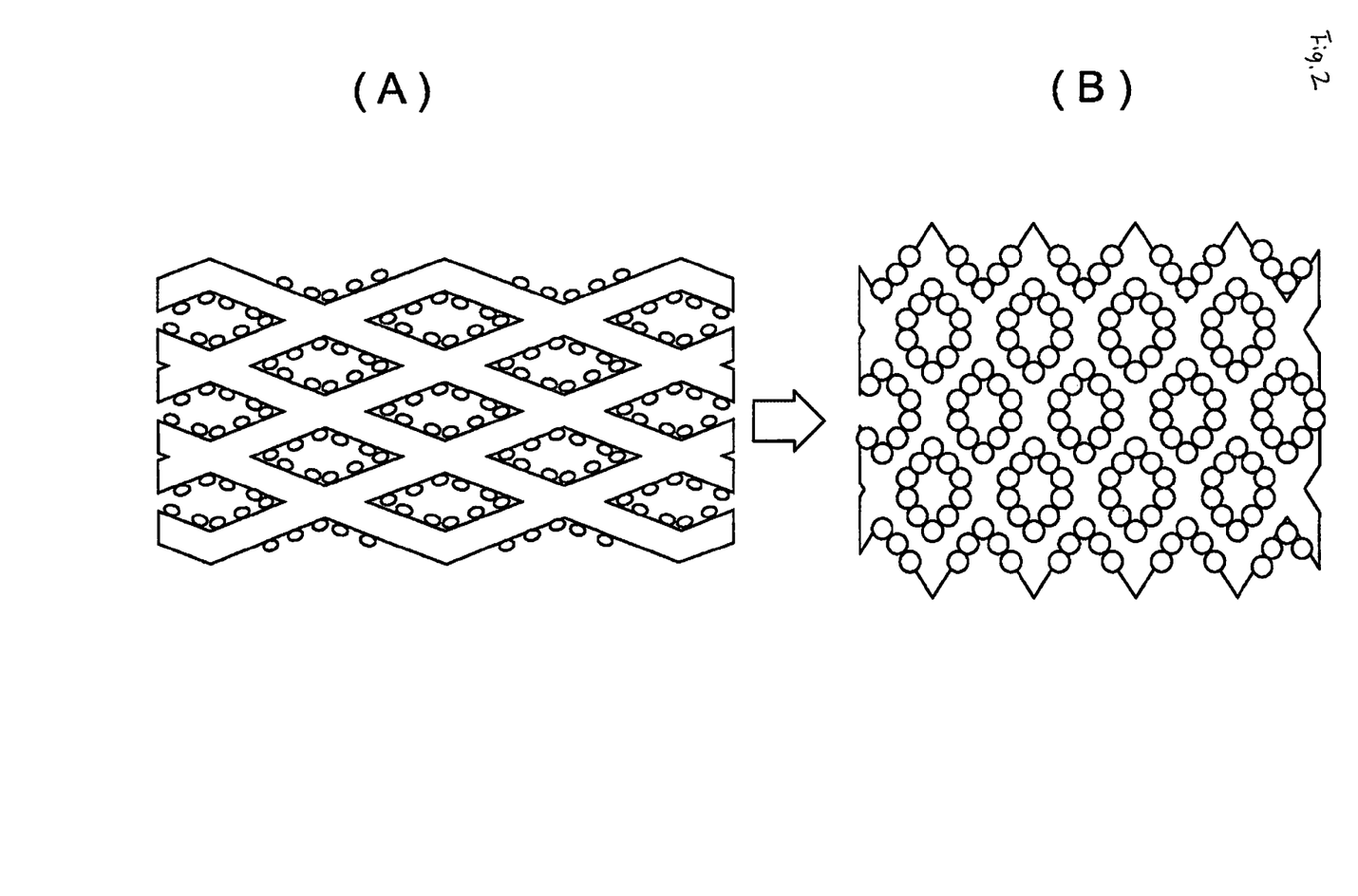
FIG. 2 shows schematic views illustrating a stent according to an embodiment of the present invention, wherein (A) is a schematic view of the stent before expansion, and (B) is a schematic view of the stent after expansion.

On the other hand, FIG. 2 shows schematic views illustrating a stent according to an embodiment of the present invention, wherein (A) is a schematic view of the stent before expansion and (B) is a schematic view of the stent after expansion. In the stent of the present invention shown in FIG. 2, a plurality of water-swellable polymer fine particles are chemically fixed on the surface of the stent in a dispersed state, or in the form of spots. As shown in (B) of FIG. 2, even when the polymer fine particles are swollen with water and further the stent is expanded and deformed, no strain is generated in the polymer fine particles, and breakage or peeling-off of the water-swollen polymer fine particles would substantially not occur, because each polymer fine particle is disposed in a dispersed state. Besides, the water-swollen polymer fine particles make contact with one another in very small areas, and the stent surface is covered with the water-swollen polymer particles.

The water-swellable polymer fine particles used in the present invention are preferably pH-responsive water swellable polymer fine particles which are swollen with water under pH 7 or more, preferably under only slightly alkaline condition which is pH 7.3 to 7.6, like in blood.

In addition, the stent according to the present invention, with the water-swellable polymer fine particles chemically fixed thereon, shows little adhesive of platelets thereto and is, therefore, excellent in antithromboyenic properties.

Besides, the stent according to the present invention is preferably coated beforehand with a coupling agent. Such a coating ensures that the water-swellable polymer fine particles are more unlikely to peel off, which means higher durability.

Now, the configuration of the stent according to the present invention will be described in detail below, but the technical scope of the invention is not to be limited to the following embodiment.

The base material of the stent according to the present invention is preferably a metal. Specific examples of the metal include nickel-titanium alloy, cobalt-chromium alloy, stainless steel, iron, titanium, aluminum, tin, and zinc-tungsten alloy. Among these metals, preferred are nickel-titanium alloy and stainless steel such as SUS316L, which are high in safety in vivo.

The shape of the stent, also, is not particularly restricted. For instance, in the mode shown in FIG. 3, the stent 1 is formed from an elastic linear (filamentous) material 2, wherein roughly rhombic elements 21 each provided with a cutout therein serve as basic units. A plurality of the roughly rhombic elements 21 are so arranged that the roughly rhombic shapes thereof are arranged and interconnected in series in the minor-axis direction, thereby forming an annular unit 22. Each annular unit 22 is connected to the adjacent annular units through linear (filamentous) elastic members 23. As a result, the plurality of annular units 22 are arranged in series in the axial direction thereof and in a partly connected state. With such a configuration, the stent 1 assumes the shape of a hollow cylindrical body which is opening at both terminal ends and extending in the longitudinal direction between the terminal ends. The stent 1 is so structured that it has the roughly rhombic cutouts and that it can be expanded and contracted in the radial direction of the hollow cylindrical body through deformation of the cutouts.

Figure 3:
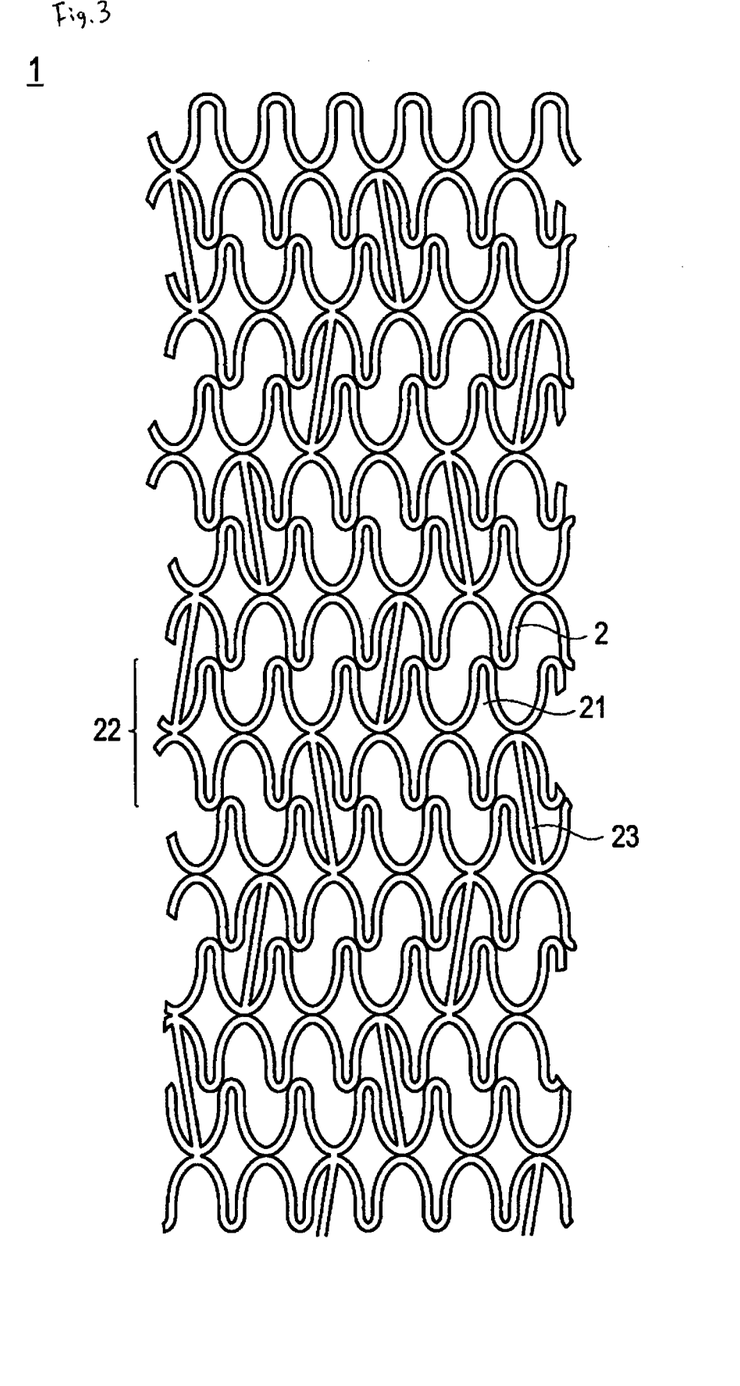
FIG. 3 is a schematic view showing an example of the shape of the stent.

It should be noted here, however, that the shape of the stent according to the present invention is not restricted to the mode shown in the figure. The stent shape widely includes those structures wherein the stent is a hollow cylindrical body opening at both terminal ends and extending in the longitudinal direction between the terminal ends, the stent is provided in its side surface with a multiplicity of cutouts providing communication between the outside surface and the inside surface of the stent, and the stent can be expanded and contracted in the radial direction of the hollow cylindrical body through deformation of the cutouts.

The sectional shape of the elastic linear material constituting the stent, also, is not particularly restricted. Examples of the applicable sectional shape include rectangles, circle, ellipses, and other polygons than rectangles.

Among the above-mentioned structures, the stent used in the present invention is preferably a so-called self-expandable stent which is formed in a roughly cylindrical hollow shape, is compressed in the center axis direction thereof when inserted into a living body and is restored into its pre-compression shape through outward expansion when put indwelling in the living body.

The method for producing the stent is not particularly restricted but may be suitably selected from the ordinarily employed production methods, according to the base material and the shape of the stent.

The stent according to the present invention, preferably, has a structure in which the metal serving as the base material is coated with a coupling agent. The coupling agent is not particularly restricted. Specific examples of the coupling agent include: silane coupling agents such as N-3-(acryloxy-2-hydroxypropyl)-3-aminopropyltriethoxysilane, 3-aminopropyltrimethoxysilane, 3-aminopropyltriethoxysilane, (3-acryloxypropyl)dimethylmethoxysilane, 3-anilinopropyltrimethoxysilane, dimethylaminopropyltrimethoxysilane, diethylaminopropyltriethoxysilane, dipropylaminopropyltrimethoxysilane, dibutylaminopropyltrimethoxysilane, monobutylaminopropyltrimethoxysilane, dioctylaminopropyltrimethoxysilane, dibutylaminopropyldimethoxysilane, dibutylaminopropylmonomethoxysilane, dimethylaminophenyltriethoxysilane, (3-acryloxypropyl)methyldimethoxysilane, (3-acryloxypropyl)trimethoxysilane, 3-(N-allylamino)propyltrimethoxysilane, allyldimethoxysilane, allyltriethoxysilane, allyltrimethoxysilane, 3-butenyltriethoxysilane, 2-(chloromethyl)allyltrimethoxysilane, methacrylamidopropyltriethoxysilane, N-(3-methacryloxy-2-hydroxypropyl)-3-aminopropyltriethoxysilane, (methacryloxydimethyl)dimethylethoxysilane, methacryloxymethyltriethoxysilane, methacryloxymethyltrimethoxysilane, methacryloxypropyldimethylethoxysilane, methacryloxypropyldimethylmethoxysilane, methacryloxypropylmethyldiethoxysilane, methacryloxypropylmethyldimethoxysilane, methacryloxypropylmethyltriethoxysilane, methacryloxypropylmethyltrimethoxysilane, methacryloxypropyltris(methoxyethoxy)silane, methoxydimethylvinylsilane, 1-methoxy-3-(trimethylsiloxy)butadiene, styrylethyltrimethoxysilane, vinyldimethylethoxysilane, vinyldiphenylethoxysilane, vinylmethyldiethoxysilane, vinylmethyldimethoxysilane, O-(vinyloxyethyl)-N-(triethoxysilylpropyl)urethane, vinyltriethoxysilane, vinyltrimethoxysilane, vinyltri-L-butoxysilane, vinyltriisopropoxysilane, vinyltriphenoxysilane, and vinyltris(2-methoxyethoxy)silane; and titanium coupling agents such as isopropyltriisostearoyl titanate, isopropyl-n-dodecylbenzenesulfonyl titanate, isopropyltris(dioctyl pyrophosphate) titanate, tetraisopropylbis(dioctyl phosphite) titanate, tetraisopropylbis(ditridecyl phosphite) titanate, tetra(2,2-diallyloxymethyl-1-butyl)bis(di-tridodecyl) phosphite titanate, bis(dioctyl pyrophosphate)oxyacetate titanate, bis(dioctyl pyrophosphate)ethylene titanate, and isopropyltri(N-aminoethyl-aminoethyl)titanate. These coupling agents may be used either singly or in combination of two or more of them.

Among the above-mentioned coupling agents, those which have both a functional group (e.g., alkoxy group) capable of forming a chemical bond with metal and a functional group (e.g., amino group) capable of forming a covalent bond with the polymer fine particle are preferred, from the viewpoint of strengthening the adhesion between the metal used as the base material of the stent and the water-swellable polymer fine particles. Specific preferable examples of such coupling agents include those silane coupling agents which have an aminoalkyl group, such as N-3-(acryloxy-2-hydroxypropyl)-3-aminopropyltriethoxysilane, 3-aminopropyltrimethoxysilane, and 3-aminopropyltriethoxysilane, and further preferable examples are 3-aminopropyltrimethoxysilane and 3-aminopropyltriethoxysilane.

The stent according to the present invention has a form wherein the plurality of water-swellable polymer fine particles are bonded to the stent surface in a dispersed state. The water-swellable polymer fine particles are not particularly restricted, and specific examples thereof include: pH-responsive water-swellable crosslinked polymers obtained by polymerization and crosslinking of a (meth)acrylamide monomer or monomers or the like; fine particles of polymers obtained by polymerization and crosslinking of a water-soluble monomer or monomers such as polyacrylic acid; fine particles of polymers obtained by crosslinking a polymeric polysaccharide or polysaccharides; fine particles of polymers obtained by crosslinking a polypeptide or polypeptides, which are amino acid polymers; fine particles of polymers of rotaxane structure in which a water-soluble polymer or polymers are crosslinked through cyclic molecules; fine particles of polymers in which a water-soluble polymer or polymers are crosslinked through a laminar clay compound; fine particles of polymers obtained by electrostatically crosslinking a water-soluble polymer having a cationic charge with a water-soluble polymer having an anionic charge; and fine particles of polymers obtained by crosslinking between water-soluble polymers having complementary hydrogen bonds by way of multi-point type hydrogen bonds.

Among others, fine particles formed from a pH-responsive water-swellable crosslinked polymer (A) obtained by subjecting a copolymer including a constituent unit derived from a (meth)acrylamide monomer (a1) and a constituent unit derived from an unsaturated carboxylic acid (a2) to crosslinking by use of a crosslinking agent (a3), are preferred for use as the above-mentioned water-swellable polymer fine particles, from the viewpoint of ensuring that the stent surface shows hydrophilic and antithrombogenic properties and that the swelling occurs only in a specific pH condition such as in blood. Now, as a preferable mode for carrying out the present invention, the pH-responsive water-swellable crosslinked polymer (A) will be described in detail below, but the technical scope of the invention is not to be limited to the following mode.

[Monomer Component of pH-Responsive Water-swellable Crosslinked Polymer]

<(Meth)Acrylamide Monomer (a1)>

The (meth)acrylamide monomer (a1) as a monomer component of the pH-responsive water-swellable crosslinked polymer (A) is not particularly restricted. Specific examples of the (meth)acrylamide monomer (a1) include (meth) acrylamide, N-methyl(meth)acrylamide, N-ethyl(meth)acrylamide, N-n-propyl(meth)acrylamide, N-isopropyl(meth)acrylamide, N-n-butyl(meth)acrylamide, N-isobutyl(meth)acrylamide, N-s-butyl(meth)acrylamide, N-t-butyl(meth)acrylamide, N,N-dimethyl(meth)acrylamide, N-ethyl-N-methyl(meth)acrylamide, N—N-diethyl(meth)acrylamide, N-methyl-N-isopropyl(meth)acrylamide, N-methyl-N-n-propyl(meth)acrylamide, N-ethyl-N-isopropyl(meth)acrylamide, N-ethyl-N-n-propyl(meth)acrylamide, N—N-di-n-propyl(meth)acrylamide, and diacetone(meth)acrylamide. These (meth) acrylamide monomers (a1) may be used either singly or in combination of two or more of them. Incidentally, in the present specification, the descriptions "(meth)acrylic acid" and "(meth)acrylamide" and the like mean acrylic acid and methacrylic acid or various derivatives thereof.

Among the above-mentioned (meth)acrylamide monomers, preferred is (meth)acrylamide, in view of their records of practical use in the orthopaedic region and the like as well as their high safety in vivo.

The unsaturated carboxylic acid (a2) as a monomer component of the pH-responsive water-swellable crosslinked polymer (A) is not particularly restricted. Specific examples of the unsaturated carboxylic acid (a2) include (meth)acrylic acid, maleic acid, fumaric acid, glutaconic acid, itaconic acid, crotonic acid, and sorbic acid. In addition, such salts as sodium salts, potassium salts and ammonium salts of the above-mentioned unsaturated carboxylic acids can also be used in preparation of the pH-responsive water-swellable crosslinked polymer (A). In the case where a salt of an unsaturated carboxylic acid is used, a constituent unit of the unsaturated carboxylic acid (a2) can be introduced into the pH-responsive water-swellable crosslinked polymer (A) by carrying out an acid treatment which will be described later. These unsaturated carboxylic acids (a2) (or their salts) may be used either singly or in combination of two or more of them.

Among others, (meth)acrylic acid and sodium (meth)acrylate are preferred, from the viewpoint of their property of showing swellability under only alkaline range which is pH 7 or more.

Incidentally, the form of the copolymer including the constituent unit derived from the (meth)acrylamide monomer (a1) and the constituent unit derived from the unsaturated carboxylic acid (a2) may be block or random.

The crosslinking agent (a3) used for the pH-responsive water-swellable crosslinked polymer (A) is not specifically restricted. Examples of the crosslinking agent (a3) include crosslinking agents (a) which have at least two polymerizable unsaturated groups, crosslinking agents (b) which have one polymerizable unsaturated group and one reactive functional group other than the polymerizable unsaturated group, and crosslinking agents (c) which have at least two reactive functional groups other than polymerizable unsaturated groups. These crosslinking agents may be used either singly or in combination of two or more of them.

In the case where only the crosslinking agent (a) is used, it suffices that copolymerization is conducted by adding the crosslinking agent (a) to the polymerization system in carrying out copolymerization of the (meth)acrylamide monomer (a1) with the unsaturated carboxylic acid (a2) (or a salt thereof). In the case where only the crosslinking agent (c) is used, it suffices that post-crosslinking, for example by heating, is conducted by adding the crosslinking agent (c) after copolymerization of the (meth)acrylamide monomer (a1) with the unsaturated carboxylic acid (a2). In the case where only the crosslinking agent (b) is used and in the case where at least two of the crosslinking agents (a), (b) and (c) are used, it suffices that copolymerization is conducted by adding the crosslinking agent(s) to the polymerization system in carrying out copolymerization of the (meth)acrylamide monomer (a1) with the unsaturated carboxylic acid (a2) and, further, post-crosslinking is conducted, for example by heating.

Specific examples of the crosslinking agent (a) having at least two polymerizable unsaturated groups include N,N'-methylenebisacrylamide, N,N'-methylenebismethacrylamide, N,N'-ethylenebisacrylamide, N,N'-ethylenebismethacrylamide, N,N'-hexamethylenebisacrylamide, N,N'-hexamethylenebismethacrylamide, N,N'-benzylidenebisacrylamide, N,N'-bis(acrylamidomethylene) urea, ethylene glycol di(meth)acrylate, polyethylene glycol di(meth)acrylate, propylene glycol di(meth)acrylate, glycerin (di or tri)acrylate, trimethylolpropane triacrylate, triallylamine, triallyl cyanurate, triallyl isocyanurate, tetraallyloxyethane, pentaerythritol triallyl ether, (poly)ethylene glycol di(meth)acrylate, (poly) propylene glycol di(meth)acrylate, trimethylolpropane tri(meth)acrylate, glycerin tri(meth)acrylate, glycerin acrylate methacrylate, ethylene oxide-modified trimethylolpropane tri(meth)acrylate, pentaerythritol hexa (meth)acrylate, triallyl cyanurate, triallyl isocyanurate, triallyl phosphate, triallylamine, poly(meth)acryloxyalkanes, (poly)ethylene glycol diglycidyl ether, glycerol diglycidyl ether, ethylene glycol, polyethylene glycol, propylene glycol, glycerin, pentaerythritol, ethylenediamine, ethylene carbonate, propylene carbonate, and glycidyl(meth)acrylate.

Specific examples of the crosslinking agent (b) having one polymerizable unsaturated group and one reactive functional group other than the polymerizable unsaturated group include hydroxyethyl(meth)acrylate, N-methylol(meth)acrylamide, and glycidyl(meth)acrylate.

Specific examples of the crosslinking agent (c) having at least two reactive functional groups other than polymerizable unsaturated groups include polyhydric alcohols (e.g., ethylene glycol, diethylene glycol, glycerin, propylene glycol, trimethylolpropane, etc.), alkanolamines (e.g., diethanolamine, etc.), and polyamines (e.g., polyethyleneimine, etc.).

Among the above-mentioned crosslinking agents, preferred are the crosslinking agents (a) having at least two polymerizable unsaturated groups, and more preferred is N,N'-methylenebisacrylamide.

The method for preparing the pH-responsive water-swellable crosslinked polymer (A) is not particularly restricted. It is preferable, however, to prepare the pH-responsive water-swellable crosslinked polymer (A) by putting the (meth)acrylamide monomer (a1), the unsaturated carboxylic acid (a2) (or their salts) and, optionally, the crosslinking agent (a3) to copolymerization and further, optionally, to post-crosslinking.

The method for copolymerization is not particularly restricted. For example, conventionally known methods such as solution polymerization, emulsion polymerization, suspension polymerization, inverse-phase suspension polymerization, thin-film polymerization, and spray polymerization, in which a polymerization initiator is used, can be used. Examples of the method for controlling the polymerization include an adiabatic polymerization method, a temperature-controlled polymerization method, and an isothermal polymerization method. Other than the methods in which polymerization is initiated by use of a polymerization initiator, there can also be adopted methods in which polymerization is initiated by irradiation with radioactive rays, electron beams, UV rays or the like. Preferred is the inverse-phase suspension polymerization method in which a polymerization initiator is used.

Examples of a solvent which can be used to form a continuous phase in carrying out the inverse-phase suspension polymerization include: aliphatic organic solvents such as n-hexane, n-heptane, n-octane, n-decane, cyclohexane, methylcyclohexane, and liquid paraffin; aromatic organic solvents such as toluene and xylene; and halogenated organic solvents such as 1,2-dichroloethane. Preferred are aliphatic organic solvents such as n-hexane, cyclohexane, and liquid paraffin. Incidentally, above-mentioned solvents can be used either singly or in combination of two or more of them.

A dispersion stabilizer may be added to the continuous phase. By appropriately selecting the kind and the use amount of the dispersion stabilizer, it is possible to control the particle diameter of the pH-responsive water-swellable polymer fine particles obtained.

Examples of the dispersion stabilizer which can be used suitably include nonionic detergents such as polyoxyethylene lauryl ether, polyoxyethylene oleyl ether, polyoxyethylene stearyl ether, sorbitan sesquioleate, sorbitan trioleate, sorbitan monolaurate, sorbitan monooleate, sorbitan monopalmitate, sorbitan monostearate, sorbitan tristearate, glycerol monostearate, grycelol monooleate, glyceryl stearate, glyceryl caprylate, sorbitan stearate, sorbitan oleate, sorbitan sesquioleate, and coconut oil fatty acid salt of sorbitan.

The dispersion stabilizer is used in an amount of preferably 0.04 to 20 mass %, more preferably 1 to 12 mass %, based on the solvent constituting the continuous phase. When the amount of the dispersion stabilizer used is less than 0.04 mass %, the polymer obtained upon polymerization may aggregate. When the amount exceeds 20 mass %, on the other hand, scattering of the particle diameter of the fine particles obtained may be large.

The concentration of the monomer component(s) in the inverse-phase suspension polymerization is not particularly limited, insofar as it is within the conventionally known range. For example, the concentration is preferably 2 to 7 mass %, more preferably 3 to 5 mass %.

Examples of the polymerization initiator to be used in the inverse-phase suspension polymerization include: persulfates such as potassium persulfate, ammonium persulfate, and sodium persulfate; peroxides such as methyl ethyl ketone peroxide, methyl isobutyl ketone peroxide, di-t-butyl peroxide, t-butylcumyl peroxide, t-butyl peroxyacetate, t-butyl peroxyisobutyrate, t-butyl peroxypivalate, and hydrogen peroxide; and azo compounds such as 2,2'-azobis[2-(N-phenylamidino)propane]dihydrochloride, 2,2'-azobis[2-(N-allylamidino)propane]dihydrochloride, 2,2'-azobis[2-[1-(2-hydroxyethyl)-2-imidazolin-2-yl]propane]dihydrochloride, 2,2'-azobis{2-methyl-N-[1,1-bis(hydroxymethyl)-2-hydroxyethyl]propionamide}, 2,2'-azobis[2-methyl-N-(2-hydroxyethyl)-propionamide], and 4,4'-azobis(4-cyanovaleric acid), which may be used either singly or in combination of two or more of them. From the viewpoint of easy availability and easiness to handle, preferred among the above-mentioned polymerization initiators are the persulfates, and more preferred are potassium persulfate, ammonium persulfate and sodium persulfate.

Incidentally, the above-mentioned polymerization initiators can also be used as a redox polymerization initiator by using them jointly with a reducing agent such as sodium sulfite, sodium hydrogensulfite, ferrous sulfate, L-ascorbic acid, and N,N,N',N'-tetramethylethylenediamine.

The amount of the polymerization initiator used is preferably 2 to 6 parts by mass, more preferably 3 to 5 parts by mass, based on 100 parts by mass of the total amount of the monomers. When the amount of the polymerization initiator is less than 2 parts by mass, the polymerization reaction itself may fail to proceed. When the amount exceeds 6 parts by mass, on the other hand, the polymer obtained may be low in molecular weight and be high in viscosity, so that the polymer may aggregate.

In the copolymerization, a chain transfer agent may be used, as required. Examples of the chain transfer agent include thiols (n-lauryl mercaptan, mercaptoethanol, triethylene glycol dimercaptan, etc.), thiolic acids (thioglycollic acid, thiomalic acid, etc.), secondary alcohols (isopropanol, etc.), amines (dibutylamine, etc.), and hypophosphites (sodium hypophosphite, etc.).

The polymerization conditions in the inverse-phase suspension polymerization are not particularly limited. For instance, the polymerization temperature may be appropriately set according to the kind of the catalyst, and is preferably 35 to 75° C., more preferably 40 to 50° C. When the polymerization temperature is below 35° C., the polymerization reaction itself may fail to proceed. When the polymerization temperature is above 70° C., on the other hand, the dispersion medium may be volatilized, worsening the dispersion state of the monomer components. The polymerization time is preferably two hours or more.

The pressure in the polymerization system is not particularly limited; the polymerization may be carried out under normal pressure (atmospheric pressure), under reduced pressure, or under increased pressure. Besides, the ambience in the polymerization system may be air or may be an inert gas such as nitrogen or argon.

In the case where the above-mentioned crosslinking agent (c) having at least two reactive functional groups other than polymerizable unsaturated groups is used as the crosslinking agent (a3), post-crosslinking may be conducted by adding the crosslinking agent (c) after completion of the polymerization reaction of the monomers.

The reaction temperature in performing the post-crosslinking depends on such factors as the kind of the crosslinking agent (a3) used, and cannot therefore be determined unconditionally; normally, the reaction temperature is 50 to 150° C. Besides, the reaction time is normally 1 to 48 hours.

In addition, a porous polymer can be obtained by suspending a pore-forming agent in the monomer solution in a supersaturated manner, in performing the copolymerization. In this case, it is preferable to use a pore-forming agent which is insoluble in the monomer solution but soluble in a cleaning solution. Preferable examples of the pore-forming agent include sodium chloride, potassium chloride, ice, sucrose, and sodium hydrogencarbonate. More preferred is sodium chloride. The concentration of the pore-forming agent in the monomer solution is preferably 5 to 50 mass %, more preferably 10 to 30 mass %.

The pH-responsive water-swellable polymer fine particles (A) obtained in this manner may, if required, be subjected to drying by heating, to shredding or the like, whereby the pH-responsive water-swellable polymer fine particles to be used in the present invention are obtained.

The shape of the pH-responsive water-swellable polymer fine particles is not particularly restricted, and may be spherical, cataclastic, indeterminate, or the like. A spherical shape is preferred.

The average particle diameter of the pH-responsive water-swellable polymer fine particles when dried is preferably 1 to 10 μm. When the average particle diameter exceeds 10 μm, fixation of the fine particles to the stent may lead to a greatly rugged surface, which may cause scattering of the endothelial cell formation speed or platelet adhesive properties. On the other hand, fine particles with an average particle diameter of less than 1 μm may be difficult to prepare satisfactorily.

The shape and the average particle diameter of the pH-responsive water-swellable polymer fine particles as above can be controlled by the conditions (the kinds of the monomers, the copolymerization temperature and time, the amount and kind of the dispersion stabilizer, etc.) for preparing the pH-responsive water-swellable polymer fine particles. Incidentally, as the average particle diameter of the fine particles when dried, the value measured by use of a Coulter counter is adopted.

In the case where a plurality of the pH-responsive water-swellable polymer fine particles configured as above are dispersed in a solvent such as hexane, preferably in a concentration of not less than 0.01 mass % and less than 0.2 mass %, each pH-responsive water-swellable polymer fine particle can be applied to the surface of the stent (coupling agent) in a dispersed state.

The pH-responsive water-swellable polymer fine particles as above are swollen with water preferably under pH 7 or more, more preferably under slightly alkaline range which is pH of 7.3 to 7.6, like in blood.

The coverage rate of the water-swellable polymer fine particles when dried is preferably 30 to 85%, more preferably 35 to 70%, and further preferably 35 to 50%. When the coverage rate is within such a range, breakage or peeling-off of the water-swellable polymer fine particles would rarely occur.

The coverage rate can be calculated as follows. The water-swellable polymer fine particles fixed on the stent are dyed by use of a dye such as Methylene Blue, and the thus dyed stent is photographed by a CCD camera, to acquire the thus obtained image as an electronic file. On the electronic file, the area of the dyed regions and the area of the non-dyed regions are measured by use of image processing software, thereby calculating the coverage rate.

In addition, the average particle diameter of the water-swellable polymer fine particles is preferably smaller than the width of the elastic linear (filamentous) material forming the stent. This is for ensuring that the water-swellable polymer fine particles can be firmly fixed to the stent.

Now, the method for producing the stent according to the present invention will be described below. The production method is not specifically restricted. It is preferable, however, that the production method includes a step (1) of coating the surface of the base material of the stent with the coupling agent, a step (2) of spraying a dispersion containing the water-swellable polymer fine particles onto the coupling agent-coated base material of the stent, a step (3) of drying the dispersion-sprayed base material of the stent by heating so as to form a thin film of the water-swellable polymer fine particles, and a step (4) of impregnating the thin film of the water-swellable polymer fine particles with an aqueous solution containing a condensation agent for effecting chemical bonding between the functional groups in the water-swellable polymer fine particles and the functional groups in the coupling agent, followed by drying by heating so as to form chemical bonds between the water-swellable polymer fine particles and the base material of the stent through the coupling agent. In addition, if required, the production method may further includes a step (5) of subjecting the stent to an acid treatment, after the step (4).

Now, the method of producing the stent according to the present invention will be described below, but the method is not to be restricted to the following mode.

In the step (1) of coating the surface of the base material of the stent with the coupling agent, the surface of the base material of the stent is coated with the coupling agent. As the coating method, there is preferably used a method in which the base material of the stent is immersed in the coupling agent.

The immersion temperature is preferably 20 to 30° C. In addition, the immersion time is preferably 5 to 60 minutes, more preferably 10 to 40 minutes. Under such immersion conditions, the surface of the base material of the stent can be coated with the coupling agent substantially evenly.

In the step (2) of spraying the dispersion containing the water-swellable polymer fine particles to the coupling agent-coated base material of the stent, the dispersion containing the plurality of the water-swellable polymer fine particles dispersed therein is sprayed onto the base material of the stent having the surface coated with the coupling agent in the step (1), whereby there can be obtained a stent coated with the water-swellable polymer fine particles in a dispersed state.

The concentration of the water-swellable polymer fine particles in the dispersion used in this step (2) is preferably not less than 0.01 mass % and less than 0.2 mass %, more preferably 0.01 to 0.1 mass %, and further preferably 0.01 to 0.05 mass %. When the concentration is less than 0.01 mass %, the concentration of the water-swellable polymer fine particles in the dispersion is too low, and it may be difficult to substantially coat the stent surface with the water-swellable polymer fine particles. When the concentration is 0.2 mass % or more, on the other hand, all the surface of the stent may be coated with the water-swellable polymer fine particles, resulting in that breakage or peel of the water-swellable polymer fine particles may occur when the stent is expanded and is deformed.

The solvent to be used in the dispersion is not particularly restricted. Examples of the solvent include water, acetone, methanol, and hexane.

The method for spraying may be, for example, a method of spraying by use of a sprayer. In the step (3) of drying the dispersion-sprayed base material of the stent by heating so as to form the thin film of the water-swellable polymer fine particles the stent coated with the plurality of water-swellable polymer fine particles in the dispersed state by the step (2) is dried by heating, to form a coating layer of the water-swellable polymer fine particles.

The drying temperature in this step (3) is preferably 40 to 80° C., more preferably 50 to 60° C. When the drying temperature is below 40° C., the solvent may be evaporated insufficiently. When the drying temperature exceeds 80° C., on the other hand, cracking or crazing of the coating film may occur.

A drying apparatus to be used in this step (3) may be an ordinarily used apparatus, for example, an oven, a hot air dryer or the like. A plurality of these drying apparatuses may be used in combination.

In the step (4) of forming chemical bonds between the water-swellable polymer fine particles and the base material of the stent through the coupling agent, the thin film of the water-swellable polymer fine particles formed in the step (3) above is impregnated with the aqueous solution containing the condensation agent for effecting chemical bonding between the functional groups in the water-swellable polymer fine particles and the functional groups in the coupling agent, followed by the drying by heating so as to form chemical bonds between the water-swellable polymer fine particles and the base material of the stent through the coupling agent.

The solvent of the solution containing the condensation agent used in this step (4) is water, but a phosphate buffer or the like may also be used suitably. In the case where the chemical bonding is effected in a phosphate buffer, for example, the phosphate buffer is so prepared as to have a pH in the range of 7.4 to 7.8.

Specific examples of the condensation agent include N-ethyl-N'-(3-diethylaminopropyl)carbodiimide, N,N'-dicyclohexylcarbodiimide, 1-methyl-2-bromopyridinium iodide, N,N'-carbonyldiimidazole, diphenylphosphorylazide, benzotriazol-1-yloxytris(dimethylamino)phosphonium hexafluorophosphate (BOP), 4-(4,6-dimethoxy[1.3.5]triazin-2-yl)-4-methylmorpholinium chloride (DMT-MM), and fluoro-N,N,N',N'-tetramethylformamidinium hexafluorophosphate (TFFH). These condensation agents may be used either singly or as a mixture of two or more of them.

The amount of the condensation agent to be used, for example in the case where the water-swellable polymer fine particles have carboxyl groups, is preferably 1 mol based on 1 mol of the total amount of the carboxyl groups.

The temperature at the time of impregnation of the thin film of the water-swellable polymer fine particles with the aqueous solution containing the condensation agent is preferably 15 to 40° C., more preferably 20 to 30° C.

The heating temperature in effecting the chemical bonding is preferably 40 to 80° C., more preferably 40 to 60° C. When the heating temperature is below 40° C., the coating film may be dried insufficiently, though the chemical bonding is achieved. When the heating temperature exceeds 80° C., on the other hand, cracking or crazing of the coating film may occur.

A heating apparatus used in effecting the chemical bonding is not specifically restricted; for example, an oven or the like may be used.

The step (5) of performing the acid treatment may include the following. In the case where a salt of the unsaturated carboxylic acid (a2) is used in copolymerization, an acid treatment may be conducted after the step (4) so that the parts of the carboxylic acid salt of the water-swellable polymer fine particles are converted into carboxyl groups. By such a treatment, it is ensured that the water-swellable polymer fine particles to be used in the present invention show pH-responsiveness, namely, is able to swell and shrink in a pH-selective manner. The conditions of the acid treatment are not specifically limited; for example, the acid treatment may be carried out in a low-pH aqueous solution such as aqueous hydrochloric acid solution, in a temperature range of preferably 15 to 60° C., for a time of preferably 1 to 24 hours.

In the case where the acid treatment is performed, drying by heating is preferably carried out after the acid treatment. In this case, the drying temperature is preferably 40 to 80° C., more preferably 40 to 60° C. When the drying temperature is below 40° C., the coating film may be dried insufficiently, though the acid treatment is achieved. When the drying temperature is above 80° C., on the other hand, cracking or crazing of the coating film may be brought about.

A drying apparatus to be used in this step (5), like that in the step (3), may be an ordinarily used device, for example, an oven, a hot air dryer or the like. A plurality of such drying apparatuses may be used in combination.

In the stent according to the present invention, the water-swellable polymer fine particles may further contain a biologically active agent. The biologically active agent is preferably at least one selected from the group composed of a substance which accelerates lysis or metabolism of thrombus or thrombus complex, a substance which restrains increase of thrombus or thrombus complex, a substance which restrains intimal thickening, a substance which accelerates endothelialization, and a substance which accelerates stabilization of unstable plaque.

Examples of the substance which accelerates lysis or metabolism of thrombus or thrombus complex include streptokinase, plasminogen activator, urokinase, staphylokinase, lumbrokinase, nattokinase and analogues thereof.

Examples of the substance which restrains increase of thrombus or thrombus complex include: antiplatelet agents represented by acetylsalicylic acid, ticlopidine, dipyridamole, cilostazol, beraprost sodium, limaprost alfadex, ethyl icosapentate, sarpogrelate hydrochloride, trapidil, clopidogrel, prasugrel and analogues thereof; GP IIb/IIIa antagonists; and anticoagulants such as heparin and warfarin potassium.

Examples of the substance which restrains intimal thickening include carcinostatic agents, immunosuppressors, antibiotics, antirheumatics, antithrombogenic agents, HMG-CoA reductase inhibitors, ACE inhibitors, calcium antagonists, antihyperlipidemia agents, anti-inflammatory agents, integrin inhibitors, antiallergic agents, antioxidants, GP IIb/IIIa antagonists, retinoid, flavonoid, carotenoid, lipid improvers, DNA synthesis inhibitors, tyrosine kinase inhibitors, antiplatelet agents, vascular smooth muscle growth inhibitors, bio-derived materials, interferon, and epithelial cells produced by genetic engineering.

Examples of the substance which accelerates endothelialization or the substance which accelerates stabilizations of unstable plaque include antithrombogenic agents, HMG-CoA reductase inhibitors, ACE inhibitors, calcium antagonists, antihyperlipidemia agents, anti-inflammatory agents, integrin inhibitors, antiallergic agents, antioxidants, GP IIb/IIIa antagonists, retinoid, flavonoid, carotenoid, lipid improvers, DNA synthesis inhibitors, tyrosine kinase inhibitors, antiplatelet agents, bio-derived materials, interferon, and epithelial cells produced by genetic engineering.

In addition, examples of the carcinostatic agent include vincristine, vinblastine, vindesine, irinotecan, pirarubicin, paclitaxel, docetaxel, and methotrexate.

Besides, examples of the immunosuppressor include sirolimus, tacrolimus, azathioprine, ciclosporine, cyclophosphamide, mycophenolate mofetil, gusperimus, and mizoribine.

In addition, examples of the antibiotic include mitomycin, adriamycin, doxorubicin, actinomycin, daunorubicin, idarubicin, pirarubicin, aclarubicin, epirubicin, peplomycin, and zinostatin stimalamer.

Besides, examples of the antirheumatic include methotrexate, sodium thiomalate, penicillamine, and lobenzarit.

In addition, examples of the antithrombogenic agent include heparin, aspirin, antithrombin preparation, ticlopidine, and hirudin.

Besides, examples of the HMG-CoA reductase inhibitor include cerivastatin, cerivastatin sodium, atorvastatin, nisvastatin, itavastatin, fluvastatin, fluvastatin sodium, simvastatin, lovastatin, and pravastatin.

In addition, examples of the ACE inhibitor include quinapril, perindopril erbumine, trandolapril, cilazapril, temocapril, delapril, enalapril maleate, lisinopril, and captopril.

Besides, examples of the calcium antagonist include nifedipine, nilvadipine, diltiazem, benidipine, and nisoldipine.

In addition, examples of the antihyperlipidemia agent include probucol.

Besides, examples of the antiallergic agent include tranilast.

In addition, examples of the'retinoid include all-trans-retinoic acid.

Besides, examples of the flavonoid and the carotenoid include catechins, particularly, epigallocatechin gallate, anthocyanin, proanthocyanidin, lycopene, and β-carotene.

In addition, examples of the tyrosine kinase inhibitor include genistein, tyrphostin, and erbstatin.

Besides, examples of the anti-inflammatory agent include salicylic acid, aspirin, acetaminophen, phenacetin, indomethacin, diclofenac sodium, piroxicam, fenoprofen calcium, ibuprofen, chlorpheniramine maleate, diflunisal, dexamethasone, clobetasol propionate, diflorasone diacetate, difluprednate, betamethasone dipropionate, diflucortolone valerate, budesonide, fluocinonide, amcinonide, halcinonide, hydrocortisone butyrate propionate, mometasone furoate, betamethasone acetate propionate, deprodone propionate, betamethasone valerate, beclomethasone dipropionate, fluocinolone acetonide, prednisolone valerate acetate, triamcinolone acetonide, flumethasone pivalate, clobetasone butyrate, hydrocortisone butyrate, prednisolone acetate, and methylprednisolone acetate.

In addition, examples of the bio-derived material include EGF (epidermal growth factor), VEGF (vascular endothelial growth factor), HGF (hepatocyte growth factor), PDGF (platelet derived growth factor), and bFGF (basic fibroblast growth factor).

Incidentally, the biologically active agents may be used as a mixture of two or more of them.

The method by which the biologically active agent is contained into the water-swellable polymer fine particles is not specifically restricted. Examples of the method include a method in which the biologically active agent is added to the dispersion containing the water-swellable polymer fine particles, and a method in which a solution or dispersion including the biologically active agent is applied to the coating layer of the water-swellable polymer fine particles, whereby the biologically active agent is contained into the water-swellable polymer fine particles.

EXAMPLES

The effect of the present invention will be described more in detail below, using the following Examples and a comparative example. It is to be noted, however, that the technical scope of the present invention is not to be limited to the following Examples.

Production Example

Production of Water-swellable Polymer Fine Particles Having an Average Particle Diameter of 2.4 μm when Dried (Before Swollen with Water)

In a 300-mL beaker were placed 150 g of liquid paraffin and 20.0 g of sorbitan sesquioleate, and the contents in the beaker was stirred by a magnetic stirrer, to prepare a continuous phase for inverse-phase suspension polymerization. A stream of nitrogen was passed to the continuous phase for 30 minutes, to remove dissolved oxygen. Separately, 3.8 g of acrylamide, 2.2 g of sodium acrylate, 0.013 g of N,N-methylenebisacrylamide, and 5.4 g of sodium chloride were weighed and placed in a 50-mL brown glass bottle, to which 19.9 g of distilled water was added. The contents in the glass bottle was stirred by a magnetic stirrer to effect dissolution, thereby preparing an aqueous monomer solution. A solution of 0.27 g of ammonium persulfate in 2.0 g of distilled water was added to the aqueous monomer solution, and the resulting solution was wholly added to the continuous-phase solvent. The resultant mixture was stirred at a rotating speed of 500 rpm, to disperse the monomer solution into the continuous-phase solvent. After stirring the contents of the beaker for 30 minutes, temperature was raised to 40° C., and 500 μL of N,N,N',N'-tetramethylethylenediamine was added to the beaker. After the stirring was continued further for one hour, the contents in the beaker was transferred into a 3-L beaker. After 1 L of dimethyl sulfoxide was added to the 3-L beaker and the contents in the beaker was stirred for five minutes, the contents in the beaker was subjected to suction filtration, to collect a powdery matter on a filter paper. The powdery matter on the filter paper was washed with 1000 mL of hexane and 1000 mL of ethanol, followed by drying under reduced pressure. The amount of the powdery product thus collected was 5.8 g. The powdery product was dispersed in ethanol, and the particle diameter of the powdery product was measured by a Coulter counter (product code: LS-230, produced by Beckman Coulter, Inc.). The average particle diameter was found to be 2.4 μm.

Example 1

Coating of a Stainless Steel-made Stent with the pH-responsive Water-swellable Polymer Fine Particles Having an Average Particle Diameter of 2.4 μm (Coverage Rate: 70%)

In a 6-mL glass-made sample bottle was sampled 2 mg of the water-swellable polymer fine particles produced in the production example above, and hexane was added thereto so that the total weight became 4 g, thereby preparing a hexane dispersion of the fine particles in a concentration of 0.05 mass %. A stent (material: stainless steel SUS316L) shaped as shown in FIG. 3 was placed in a 2% ethanol solution of 3-aminopropyltriethoxysilane (KBE903, produced by Shin-Etsu Chemical Co., Ltd.), which is a silane coupling agent, at room temperature (23° C.) for 30 minutes, followed by drying. Next, the 0.05 mass % hexane dispersion of the fine particles prepared above was sprayed onto the stent by use of a sprayer, and drying by heating was conducted in an oven at 70° C. for 48 hours. The stent coated with the water-swellable polymer fine particles was immersed for 10 seconds in a solution obtained by dissolving 30 mg of DMT-MM (produced by Kokusan Chemical Co., Ltd.) as a condensation agent in 9 g of a phosphate buffered saline. After the immersion, drying by heating was conducted in an oven at 70° C. for 12 hours, to obtain a stent wherein the water-swellable polymer fine particles were bonded to the stent through the silane coupling agent. Further, the stent was kept in contact with 0.1. N hydrochloric acid at 25° C. for 24 hours, then washed with distilled water, and was dried by heating in an oven at 70° C. for 12 hours, to impart a pH-responsive property to the water-swellable polymer fine particles. The water-swellable polymer fine particles fixed on the stent were dyed by use of a 0.1% aqueous solution of Methylene Blue. The thus dyed stent was photographed by a CCD camera, and the image obtained was acquired as an electronic file. On the electronic file, the area of the dyed regions and the area of the non-dyed regions were measured by use of image processing software, to calculate the coverage rate. The coverage rate was 70%.

Example 2

Coating of Stainless Steel-made Stent with the pH-responsive Water-swellable Polymer Fine Particles Having an Average Particle Diameter of 2.4 µm (Coverage Rate: 35%)

In a 6-mL glass-made sample bottle was sampled 1 mg of the water-swellable polymer fine particles produced in the production example above, and hexane was added thereto so that the total weight became 4 g, thereby preparing a hexane dispersion of the fine particles in a concentration of 0.025 mass %. A stent (material: stainless steel SUS316L) shaped as shown in FIG. 3 was placed in a 2% ethanol solution of 3-aminopropyltriethoxysilane (KBE903, produced by Shin-Etsu Chemical Co., Ltd.), which is a silane coupling agent, at room temperature (23° C.) for 30 minutes, followed by drying. Next, the 0.025 mass % hexane dispersion of the fine particles prepared above was sprayed onto the stent by use of a sprayer, and drying by heating was conducted in an oven at 70° C. for 48 hours. The stent coated with the water-swellable polymer fine particles was immersed for 10 seconds in a solution obtained by dissolving 30 mg of DMT-MM (produced by Kokusan Chemical Co., Ltd.) as a condensation agent in 9 g of a phosphate buffered saline. After the immersion, drying by heating was conducted in an oven at 70° C. for 12 hours, to obtain a stent wherein the water-swellable polymer fine particles were bonded to the stent through the silane coupling agent. Further, the stent was kept in contact with 0.1 N hydrochloric acid at 25° C. for 24 hours, then washed with distilled water, and was dried by heating in an oven at 70° C. for 12 hours, to impart a pH-responsive property to the water-swellable polymer fine particles. The water-swellable polymer fine particles fixed on the stent were dyed by use of a 0.1% aqueous solution of Methylene Blue. The thus dyed stent was photographed by a CCD camera, and the image obtained was acquired as an electronic file. On the electronic file, the area of the dyed regions and the area of the non-dyed regions were measured by use of image processing software, to calculate the coverage rate. The coverage rate was 35%.

(Evaluation 1: Balloon Inflation Test)

Figure 4:
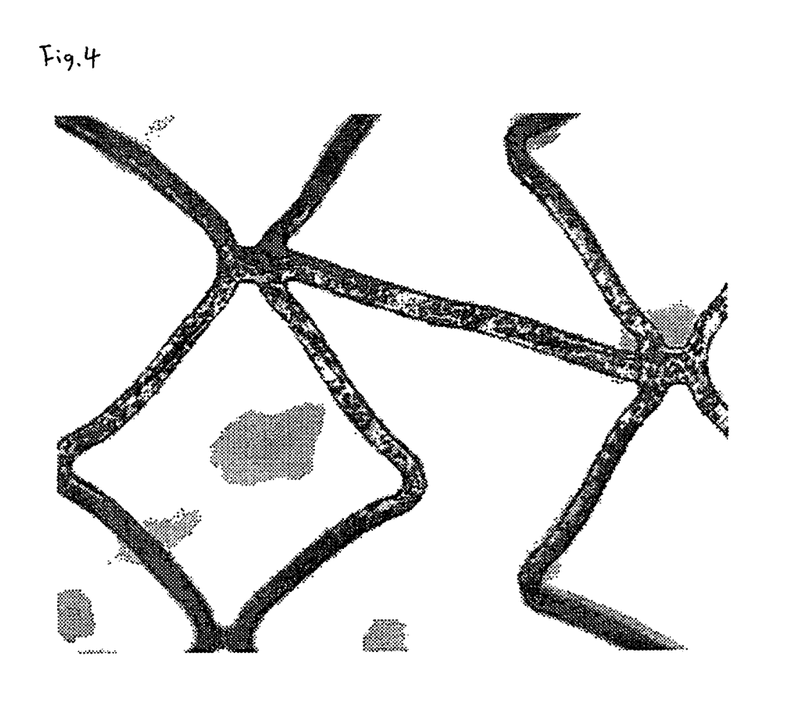
FIG. 4 is a photomicrograph, in observation with a CCD camera, of a stent obtained in Example 1 and dyed.

The stent obtained in Example 1 was crimped on a balloon catheter, and the assembly was immersed in a phosphate buffered saline for five minutes, followed by inflating the balloon to expand the stent. Then, the balloon was deflated, the stent was taken out, and was placed in a 0.1% aqueous solution of Methylene Blue, whereby the water-swellable polymer fine particles applied to the stent surface were dyed. The thus dyed stent was photographed by a CCD camera, the photograph being shown in FIG. 4. As shown in FIG. 4, on the stent of Example 1, no peeled fragment or the like of the polymer fine particles was observed.

(Evaluation 2: Platelet Adhesive Test)

Blood was drawn from a human elbow vein, with addition of 3.8% sodium citrate in an amount ratio of 1/9 by volume. The blood sample obtained was centrifuged at 1200 rpm for five minutes, to separate PRP (platelet-rich plasma), and the number of platelets was measured by an automated multi-channel blood cell analyzer (product code: Sysmex XE-2100, produced by Sysmex Corporation). After the PRP was separated out, the blood sample was further centrifuged at 3000 rpm for 10 minutes, to separate PPP (platelet-poor plasma). The PRP was diluted with the PPP, to control the number of platelets to 105. The diluted PRP, in an amount of 0.2 mL each, was dropped on the stent obtained in Example 1, the stent obtained in Example 2, and a Comparative Example stent (material: stainless steel SUS316L) which was shaped as shown in FIG. 3 but on which the water-swellable polymer fine particles were not fixed. The stents were left at room temperature (23° C.) for 30 minutes, and was lightly washed twice with phosphate buffered saline (PBS). Then, the stents were put to fixation in 1 mass % glutaraldehyde-containing PBS solution at 4° C. a whole day and night. Subsequently, the stents were washed with PBS, and dried. Each of the stents was put to ion sputtering, observation under a scanning electron microscope (SEM), and photographing (×1000, 5 visual fields). From the photographs, the number of platelets adhered to the stent was calculated. The results are shown in Table 1 below.

TABLE 1

|  | Number of adhered platelets |
|---|---|
| Example 1 | 10 |
| Example 2 | 15 |
| Comparative Example | 100 |

As shown in Table 1 above, it was found difficult for platelets to be adhered to the stents of Examples 1 and 2 compared with the stent of Comparative Example.

Description of Reference Numerals

1 . . . Stent
2 . . . Elastic linear material
21 . . . Roughly rhombic element
22 . . . Annular unit
23 . . . Linear elastic member

The invention claimed is:

1. A stent wherein a plurality of pH-responsive water-swellable polymer fine particles that are swellable under pH 7 or more are chemically fixed on the stent surface in a dispersed state, and the pH-responsive water-swellable polymer fine particles are fine particles formed from a pH-responsive water-swellable crosslinked polymer (A) obtained by subjecting a copolymer including a constituent unit derived from a (meth) acrylamide monomer (a1) and a constituent unit derived from an unsaturated carboxylic acid (a2) to crosslinking by use of a crosslinking agent (a3).

2. The stent according to claim 1, wherein the water-swellable polymer fine particles have a coverage rate of 30 to 85 % when dried.

3. The stent according to claim 1, wherein the water-swellable polymer fine particles have an average particle diameter of 1 to 10 µm when dried.

4. The stent according to claim 1, wherein the average particle diameter of the water-swellable polymer fine particles when dried is smaller than the width of an elastic linear material forming the stent.

5. The stent according to claim 1, wherein the water-swellable polymer fine particles further include a biologically active agent.

6. The stent according to claim 5, wherein the biologically active agent is at least one selected from the group composed of a substance which accelerates lysis or metabolism of thrombus or thrombus complex, a substance which restrains increase of thrombus or thrombus complex, a substance which restrains intimal thickening, a substance which accelerates endothelialization, and a substance which accelerates stabilization of unstable plaque.

* * * * *